US00PP24096P3

(12) United States Plant Patent
Fear et al.

(10) Patent No.: US PP24,096 P3
(45) Date of Patent: Dec. 17, 2013

(54) STRAWBERRY PLANT NAMED 'DRISSTRAWTHIRTY'

(50) Latin Name: *Fragaria×ananassa*
Varietal Denomination: DrisStrawThirty

(75) Inventors: Carlos D. Fear, West Malling (GB); Matthias D. Vitten, Aptos, CA (US); Michael D. Ferguson, Moorpark, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 13/506,410

(22) Filed: Apr. 17, 2012

(65) Prior Publication Data

US 2013/0276183 P1 Oct. 17, 2013

(51) Int. Cl.
*A01H 5/00* (2006.01)

(52) U.S. Cl.
USPC ..... Plt./208

(58) Field of Classification Search
USPC ..... Plt./208, 209
See application file for complete search history.

*Primary Examiner* — Kent L Bell

(74) *Attorney, Agent, or Firm* — Jondle Plant Sciences Division of Swanson & Bratschun, L.L.C.

(57) ABSTRACT

A new and distinct variety of strawberry plant named 'DrisStrawThirty' particularly characterized by high yield, dark red fruit color, and large fruit with medium sweetness is disclosed.

3 Drawing Sheets

Genus and species: *Fragaria×ananassa.*
Variety denomination: 'DrisStrawThirty'.

BACKGROUND OF THE NEW PLANT

The present invention relates to a new and distinct strawberry variety designated 'DrisStrawThirty' and botanically known as *Fragaria×ananassa*. This new strawberry variety was discovered in Avitorejo, Spain in February 2007 and originated from a cross between the proprietary female parent 'DrisStrawTwenty' (U.S. Plant Pat. No. 23,383) and the proprietary male parent '197M167' (unpatented). A single plant was selected for asexual propagation via tissue culture and vegetative cuttings in Palencia, Spain in 2007.

'DrisStrawThirty' underwent further testing in Spain for five years (2007-2011). The present invention has been found to retain its distinctive characteristics through successive asexual propagations via stolons and tissue culture.

Plant Breeder's Rights for this variety have not been applied for. 'DrisStrawThirty' has not been made publicly available or sold more than one year prior to the filing date of this application.

SUMMARY OF THE INVENTION

The following are the most outstanding and distinguishing characteristics of this new cultivar when grown under normal horticultural practices in Avitorejo, Spain.

1. High yield;
2. Dark red fruit color; and
3. Large fruit with medium sweetness.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from six-month-old plants.

DESCRIPTION OF THE NEW VARIETY

Figure 1:
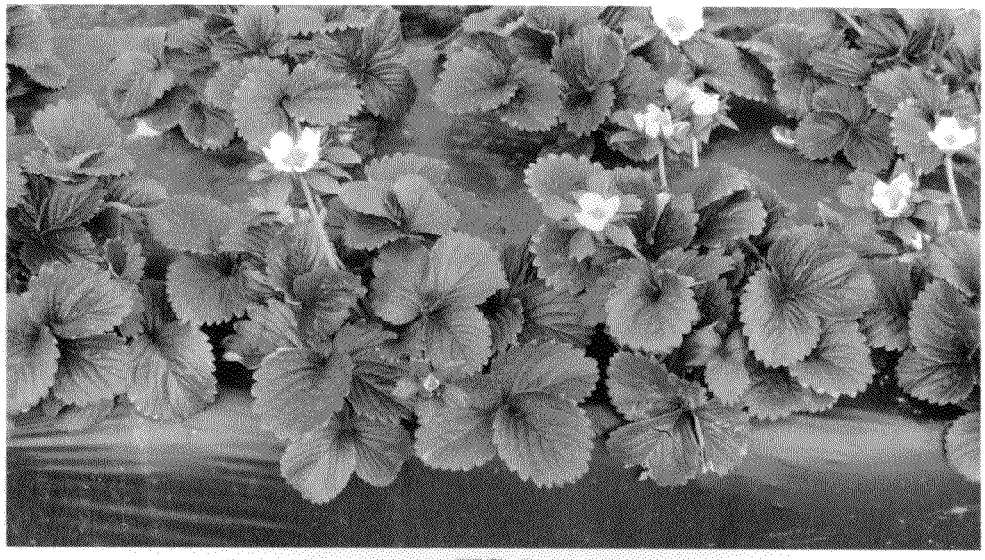
FIG. 1 shows overall plant habit including fruit at various stages of development.
Figure 2:
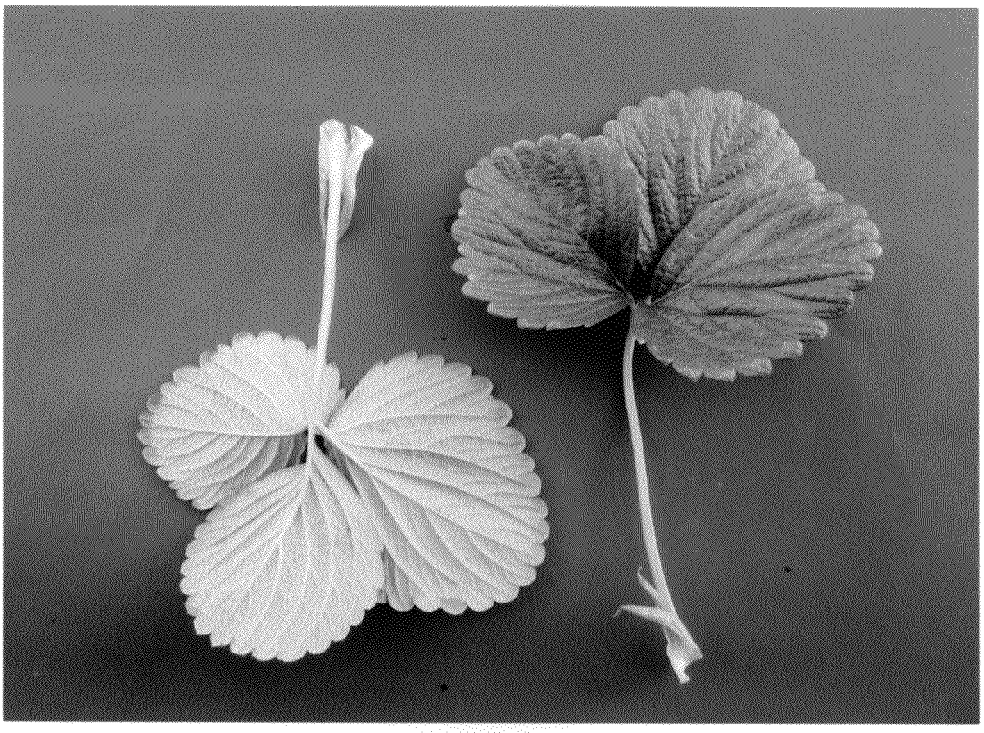
FIG. 2 shows upper and lower surfaces of the leaves of the plant with three leaflets.
Figure 3:
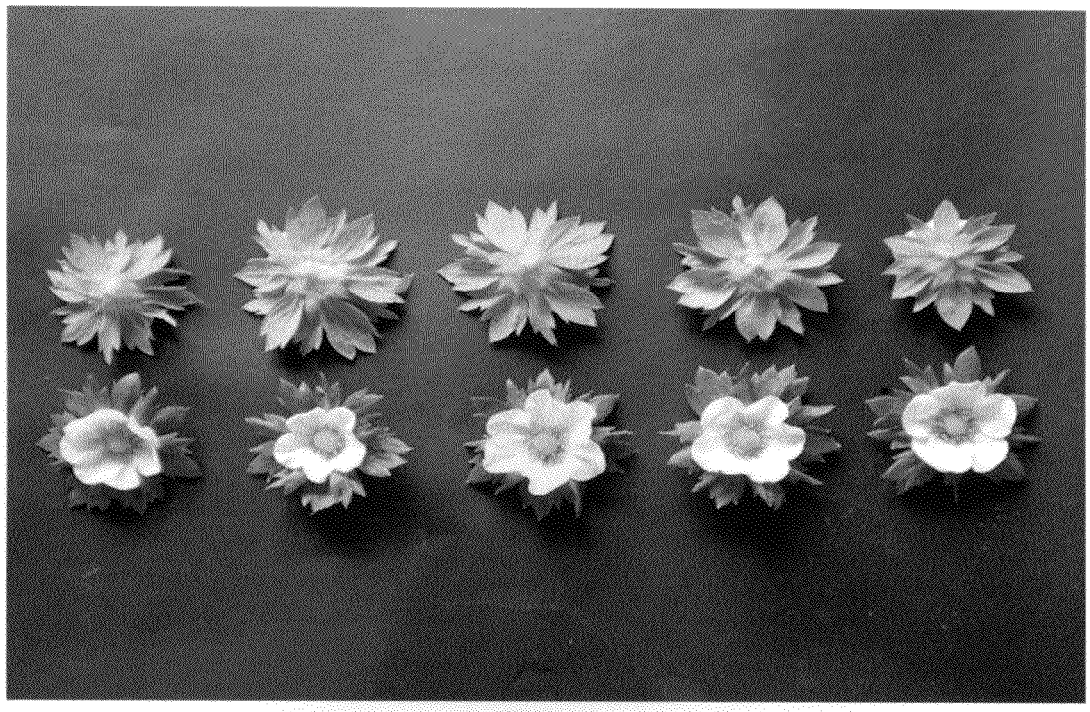
FIG. 3 shows both upper and lower surfaces of the flowers.
Figure 4:
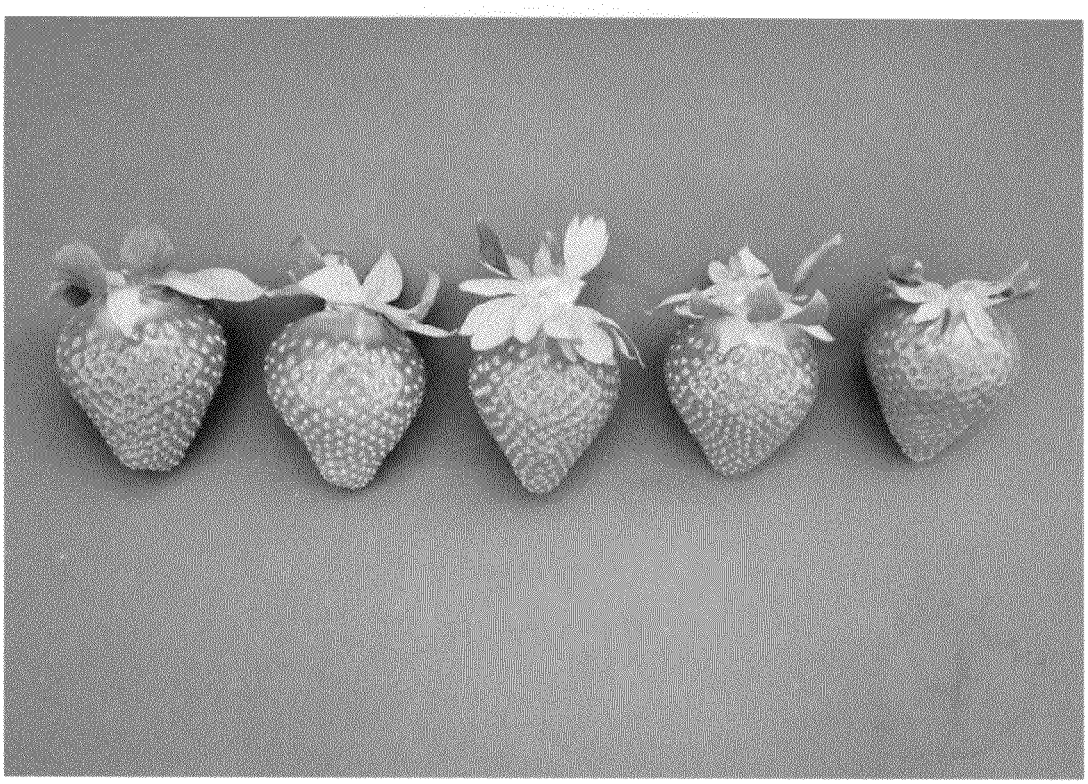
FIG. 4 shows the whole fruit.
Figure 5:
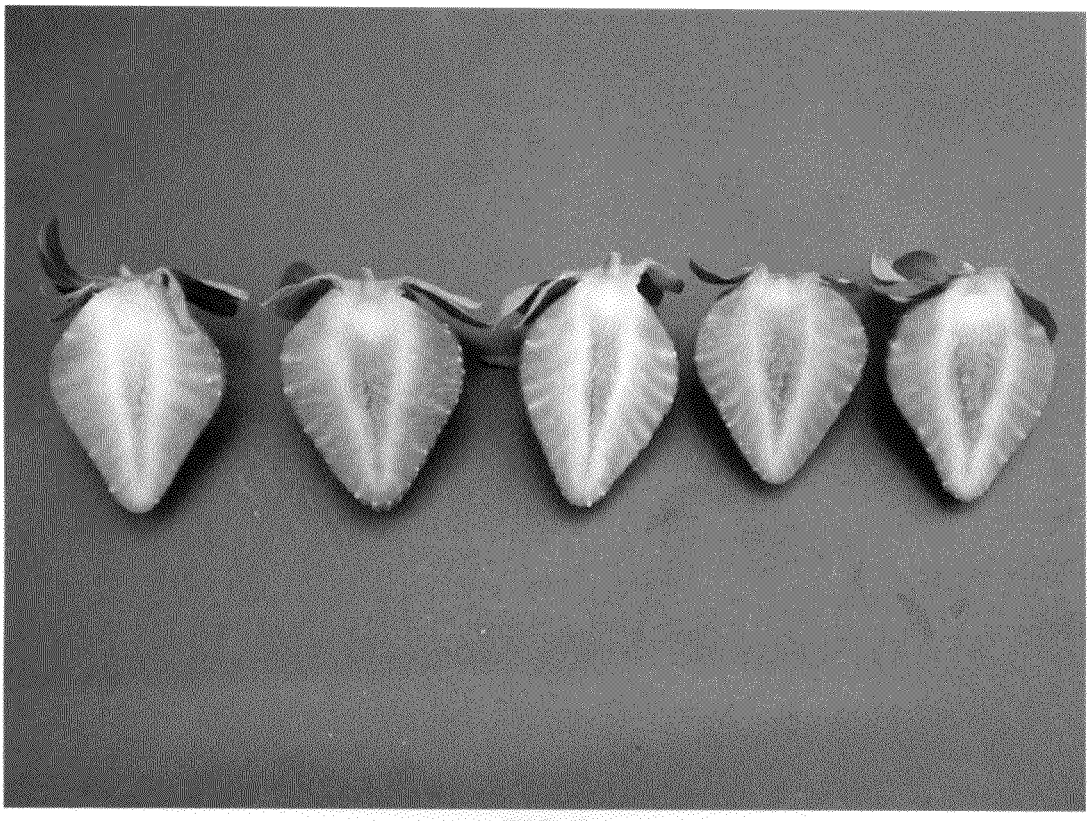
FIG. 5 shows the fruit in longitudinal cross-section.

The following detailed descriptions set forth the distinctive characteristics of 'DrisStrawThirty'. The data which define these characteristics is based on observations taken in Avitorejo, Spain from 2010 to 2011. This description is in accordance with UPOV terminology. Color designations, color descriptions, and other phenotypical descriptions may deviate from the stated values and descriptions depending upon variation in environmental, seasonal, climatic, and cultural conditions. 'DrisStrawThirty' has not been observed under all possible environmental conditions. The botanical description of 'DrisStrawThirty' was taken from six-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary, 2nd* edition by James G. Harris and Melinda Woolf Harris, unless where otherwise defined.

DETAILED BOTANICAL DESCRIPTION OF THE PLANT

Classification:

*Species.*—*Fragaria×ananassa.*
*Common name.*—Strawberry.
*Denomination.*—'DrisStrawThirty'.

Parentage:
*Female parent*.—The proprietary variety 'DrisStrawTwenty' (U.S. Plant Pat. No. 23,383).
*Male parent*.—The proprietary variety '197M167' (unpatented).

Plant:
*Height*.—40.1 cm.
*Diameter*.—46.9 cm.
*Number of crowns/plant*.—3.
*Habit*.—Upright.
*Density of individual plant*.—Medium.
*Vigor* (*health and hardiness of plant*).—Strong.

Terminal leaflets:
*Size*.—Large. Length: 8.77 cm. Width: 7.94 cm. Length/width ratio: 1.1.
*Number of teeth/terminal leaflet*.—19.
*Shape of teeth*.—Obtuse — serrate to crenate.
*Color*.—Upper surface: RHS N137C (Dark green). Lower surface: RHS 191A (Medium greyed-green).
*Shape in cross section*.—Slightly concave.
*Blistering*.—Weak.
*Glossiness*.—Medium.
*Number of leaflets*.—Three only.
*Shape*.—Orbicular.
*Base shape*.—Acute.
*Apex descriptor*.—Rounded.
*Variegation*.—Absent.
*Margin*.—Serrate.
*Margin profile*.—Revolute.

Petiole:
*Length*.—30.7 cm.
*Diameter*.—4.02 mm.
*Pubescence*.—Absent or very sparse.
*Pose of hairs*.—Slightly upwards.
*Color*.—RHS 144C (Light yellow-green).

Petiolule:
*Length*.—13.18 mm.
*Diameter*.—2.16 mm.
*Bract frequency*.—0.
*Color*.—RHS 144C (Light yellow-green).

Stipule:
*Length*.—40.8 mm.
*Width*.—9.94 mm.
*Pubescence*.—Dense.
*Stipule anthocyanin coloration*.—Weak; RHS 143C (Medium green).

Stolon:
*Stolon anthocyanin coloration*.—Medium; RHS 144B (Medium yellow-green).
*Number*.—Many.
*Average number of daughter plants*.—25.
*Thickness*.—Medium.
*Density of pubescence*.—Medium.

Inflorescence:
*Position relative to foliage*.—Level.
*Number of flowers per inflorescence*.—Few; 3.3.
*Natural flowering season*.—Between early December until late April when planted in September in Spain.
*Time of flowering* (*50% of plants at first flower*).—Medium.
*Flower size*.—Large.
*Diameter*.—25.87 mm.
*Petals*.—Shape: Orbicular. Apex: Rounded. Base: Convex. Margin: Entire. Spacing: Overlapping Length: 14.81 mm. Width: 14.73 mm. Length/width ratio: 1.0 (As long as broad). Typical and observed petal number per flower: 6. Color (both upper and lower surfaces): RHS 155C (White).
*Calyx*.—Diameter: 40.42 mm. Diameter relative to corolla: Larger. Inner calyx diameter relative to outer: Smaller. Insertion of calyx: Set above fruit — raised. Pose of calyx segments: Spreading — outwards. Size of calyx in relation to fruit: Slightly larger. Adherence of calyx: Weak.
*Sepal*.—Shape: Elliptical. Apex: Truncate. Margin: Entire. Length: 18.90 mm. Width: 9.68 mm. Typical and observed sepal number per flower: 6.
*Receptacle color*.—RHS N144B (Light yellow-green).
*Stamen*.—Present. Anther color: RHS 153C (Light yellow-green).
*Pedicel*.—Attitude of hairs: Slightly upwards.

Fruiting truss:
*Length*.—Medium; 35.0 cm.
*Diameter at base of truss*.—3.46 mm.
*Number of berries per fruiting truss*.—3.
*Attitude at first picking*.—Semi-erect.
*Color at base of truss*.—RHS 143C (Medium green).

Fruit:
*Relative fruit size*.—Large.
*Length*.—44.46 mm.
*Width*.—36.79 mm.
*Length/width ratio*.—1.2 (Longer than broad).
*Fruit hollow length*.—38.85 mm.
*Fruit hollow width*.—11.64 mm.
*Fruit hollow length/width ratio*.—3.3 (Longer than broad).
*Fruit hollow center* (*cavity*).—Medium.
*Weight* (*per individual berry*).—30.3 g.
*Predominant fruit shape*.—Conical.
*Difference in shape between primary and secondary fruits*.—None or very slight (mid-season).
*Evenness of fruit surface*.—Even or very slightly uneven.
*Fruit skin color*.—RHS 45A (Dark red).
*Evenness of fruit color*.—Slightly uneven.
*Fruit glossiness*.—Strong.
*Achenes*.—Insertion of achenes: Level with surface. Coloration (sunward side of berry): RHS 173B (Medium greyed-orange). Coloration (shaded side of berry): RHS 178B (Dark greyed-red). Number per berry: 370. Weight (weight of achenes divided by total # seed): 0.00042 g. Width of band without achenes: Broad.
*Firmness of flesh* (*when fully ripe*).—Soft.
*Color of flesh* (*excluding core*).—RHS 44A (Medium red).
*Color of core*.—RHS 34B (Medium orange-red).
*Evenness of flesh color*.—Slightly uneven.
*Distribution of flesh color*.—Marginal and central.
*Sweetness*.—Medium.
*Acidity*.—Medium.
*Texture when tasted*.—Fine.
*Type of bearing*.—Not everbearing — not remontant.
*Grams of fruit/plant*.—900.0 g.
*Harvest interval*.—Late December — late May.
*Harvest maturity*.—Mid-season.

Disease, pest, and stress resistance:
*Botrytis fruit rot*.—Moderately susceptible.
*Powdery mildew*.—Moderately resistant.
*Drought*.—Moderately susceptible.

*High temperatures*.—Moderately susceptible.
*Wind*.—Moderately resistant.

COMPARISON WITH PARENTAL AND COMMERCIAL VARIETIES

When 'DrisStrawThirty' is compared to the proprietary female parent 'DrisStrawTwenty' (U.S. Plant Pat. No. 23,383), 'DrisStrawThirty' has fruit with dark red skin color, inflorescence positioned level with the foliage, three berries per fruiting truss, and few flowers, whereas 'DrisStrawTwenty' has fruit with medium red skin color, inflorescence positioned above the foliage, one berry per fruiting truss, and many flowers. Additionally, 'DrisStrawThirty' has a higher fruit yield and greater individual berry weight than 'DrisStrawTwenty'.

When 'DrisStrawThirty' is compared to the proprietary male parent '197M167' (unpatented), 'DrisStrawThirty' has consistently better shelf life after shipping than '197M167'.

When 'DrisStrawThirty' is compared to the commercial variety 'DrisStrawEight' (U.S. Plant Pat. No. 20,735), 'DrisStrawThirty' has a strong vigor, achenes inserted level with the fruit surface, and is not everbearing, whereas 'DrisStrawEight' has a medium vigor, achenes inserted below the fruit surface, and is partially everbearing.

When 'DrisStrawThirty' is compared to the commercial variety 'DrisStrawSixteen' (U.S. Plant Pat. No. 22,247), 'DrisStrawThirty' has no difference or a very slight difference in shape between primary and secondary fruits, a broad band without achenes, and is moderately resistant to Powdery Mildew, whereas 'DrisStrawSixteen' has a marked difference in shape between primary and secondary fruits, a narrow band without achenes, and is moderately susceptible to Powdery Mildew.

We claim:

1. A new and distinct variety of strawberry plant named 'DrisStrawThirty' as described and shown herein.

* * * * *